(12) United States Patent
Caizza et al.

(10) Patent No.: US 6,730,059 B2
(45) Date of Patent: May 4, 2004

(54) MEDICAL NEEDLE ASSEMBLIES

(75) Inventors: Richard James Caizza, Vernon, NJ (US); Paul G. Alchas, Wayne, NJ (US); Alfred Wesley Prais, Hewitt, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/140,950

(22) Filed: May 9, 2002

(65) Prior Publication Data

US 2003/0125675 A1 Jul. 3, 2003

Related U.S. Application Data

(60) Provisional application No. 60/344,303, filed on Dec. 28, 2001.

(51) Int. Cl.$^7$ .............................. A61M 5/00; A61M 5/31
(52) U.S. Cl. ........................ 604/110; 604/240; 604/241; 128/919
(58) Field of Search ................................ 604/110, 192, 604/263, 272, 198, 240–243; 128/919

(56) References Cited

U.S. PATENT DOCUMENTS

| | | | |
|---|---|---|---|
| 1,567,463 A | 12/1925 | Platt et al. | 604/241 |
| 2,604,890 A | 7/1952 | Burnside | 128/218 |
| 3,119,391 A | 1/1964 | Harrison | 128/221 |
| 3,194,237 A | 7/1965 | Rubin | 128/253 |
| 3,512,520 A | 5/1970 | Cowan | 128/2 |
| 3,890,972 A | 6/1975 | Standley et al. | 128/220 |
| 3,905,371 A | 9/1975 | Stickl et al. | 128/253 |
| 3,948,261 A | 4/1976 | Steiner | 128/253 |
| 4,740,205 A | 4/1988 | Seltzer et al. | 604/192 |
| 4,822,343 A | 4/1989 | Beiser | 604/187 |
| 4,838,877 A | 6/1989 | Massau | 604/272 |
| 4,904,244 A | 2/1990 | Harsh et al. | 604/187 |
| 4,907,600 A | 3/1990 | Spencer | 128/764 |
| 4,950,253 A | 8/1990 | Jacobs | 604/218 |
| 4,993,426 A | 2/1991 | Spencer | 128/763 |
| 5,030,205 A | * 7/1991 | Holdaway et al. | 604/164.02 |
| 5,064,411 A | * 11/1991 | Gordon, III | 604/48 |
| 5,201,716 A | 4/1993 | Richard | 604/187 |
| 5,205,833 A | 4/1993 | Harsh et al. | 604/240 |
| 5,217,436 A | 6/1993 | Farkas | 604/187 |
| 5,246,423 A | * 9/1993 | Farkas | 604/110 |
| 5,407,431 A | * 4/1995 | Botich et al. | 604/110 |
| 5,458,580 A | 10/1995 | Hajishoreh | 604/240 |
| 5,562,625 A | 10/1996 | Stefancin, Jr. | 604/110 |
| 5,588,966 A | 12/1996 | Atsumi | 604/110 |
| 5,616,136 A | 4/1997 | Shillington et al. | 604/240 |
| 5,632,728 A | 5/1997 | Hein | 604/46 |
| 5,637,101 A | 6/1997 | Shillington | 604/242 |
| 5,695,477 A | 12/1997 | Sfikas | 604/241 |
| 5,713,876 A | 2/1998 | Bogert et al. | 604/243 |
| 6,096,010 A | 8/2000 | Walters et al. | 604/207 |
| 6,241,710 B1 | 6/2001 | Van Tassel et al. | 604/272 |
| D471,980 S | * 3/2003 | Caizza | D24/130 |
| D476,418 S | * 6/2003 | Sprieck et al. | D24/130 |

FOREIGN PATENT DOCUMENTS

WO    WO 94/26333    11/1994

* cited by examiner

*Primary Examiner*—Brian L. Casler
*Assistant Examiner*—Catherine S. Williams
(74) *Attorney, Agent, or Firm*—Webb Ziesenheim Logsdon Orkin & Hanson, P.C.

(57) ABSTRACT

A medical needle device which is reusable and cooperates with a disposable needle assembly. The medical needle device includes a holder, a needle assembly, and an ejector rod cooperating with the holder. The needle assembly includes a needle hub and needle. The holder has a proximal end and a distal end and defines an opening extending therethrough. The distal end has a hub socket for receiving the hub of the needle, with the needle hub received in the socket. The ejector extends into the opening from the proximal end of the holder. The ejector rod is slidably received in the holder and has a distal end configured to engage the needle hub, and a proximal end extending outward from the holder. The ejector rod is used to eject the needle assembly from the holder.

27 Claims, 10 Drawing Sheets

MEDICAL NEEDLE ASSEMBLIES

CROSS-REFERENCE TO RELATED APPLICATION

This application claims priority from U.S. Provisional Patent Application Serial No. 60/344,303, filed Dec. 28, 2001 and entitled, "E-Z Holder/Dispenser for Medical Device."

BACKGROUND OF THE INVENTION

1. Field of the Invention

The present invention relates to a medical needle device for use in medical procedures and, more particularly, a reusable unit dose needle device having a disposable needle assembly.

2. Description of Related Art

Disposable medical devices with piercing elements are well-known for administering medications such as a vaccine or withdrawing fluid from the human body. Such devices include hypodermic needles, blood collecting needles, fluid handling needles, and needles used in the administration of vaccines. These devices require safe and convenient handling to minimize exposure to bloodborne pathogens. Typically, disposable medical devices are discarded in their entirety. For example, numerous devices have shielding mechanisms for shielding the needle cannula after use. Many of these devices are complex to use and costly to manufacture. In addition, the disposal of the entire device is inefficient and costly.

One application for such a device is in the administration of vaccines or other active pharmaceutical ingredients that are applied through the skin. Bifurcated or forked-end needles are well-known for providing a simple and effective means for a medical practitioner to administer a vaccine. During use, the bifurcated tip of the bifurcated needle is placed into contact with either a dried or liquid substance, which adheres to the bifurcated needle tip. The bifurcated needle tip is then placed into contact with the skin of the patient. The skin is either scratched or pierced with the needle tip so that the vaccination material may be absorbed into the skin of the patient. An alternative method of delivering the vaccine includes placing a drop of the vaccine onto the skin of the patient and piercing the skin with the bifurcated needle tip through a drop of the vaccine. A standard pointed needle tip may also be used when the drop of vaccine is applied directly to the skin of the patient.

The bifurcated needle is considered a significant medical advancement because it allows more people to be vaccinated with less serum. This has been especially important for those living in less developed areas because of the efficient and easy to use design, as well as the ease of replication. Vaccination effectiveness, however, is reduced if the bifurcated needle is reused too many times. More importantly, reuse of such vaccination needles exposes patients to the risk of transmission of infectious diseases through percutaneous contact through the skin.

Additionally, medical care workers using traditional vaccine needles are at an increased risk of exposure to infectious disease due to the design of such needles, which makes them difficult to handle. In particular, bifurcated needles used to administer vaccinations are not traditionally sterilized or packaged in a single-use container that would enable convenient storage and use. Such needles have traditionally been difficult to handle because they typically do not include a hub attached to the opposite end of the needle tip, and typically do not include any sort of holder for carrying the needle cannula prior to use or any sort of shielding for covering the needle tip after use.

In view of the foregoing, a need exists for a reusable medical needle device in which a disposable needle and hub assembly may be used. A specific need exists for a reusable medical needle device that is capable of carrying a bifurcated needle and hub assembly that is quickly and easily disposable after use, such as after use in a vaccination procedure.

SUMMARY OF THE INVENTION

The above needs are satisfied with a medical needle device made in accordance with the present invention. The medical needle device includes a holder, a needle assembly, and an ejector rod cooperating with the holder. The holder has a proximal end and a distal end, and defines an opening extending from the proximal end to the distal end. The distal end has a socket for receiving a needle hub. The needle assembly includes a needle hub and a needle. The needle hub is received in the socket. The ejector rod extends into the opening from the proximal end of the holder. The ejector rod is slidably received in the holder and has a distal end configured to communicate with the needle hub. The ejector rod has a proximal end extending outward from the holder. Movement of the ejector rod into the holder causes the distal end of the ejector rod to bias the needle hub outward from the socket, thereby ejecting the needle assembly from the holder. Desirably, the needle is a bifurcated needle, and is connected to the hub by a medical grade adhesive. A proximal end of the needle hub may define a luer cavity.

The holder may define an internal rib extending into the opening. A bushing is adjacent the distal end of the ejector rod, and may be received about the distal end of the ejector rod between the needle hub and internal rib. Preferably, the needle hub and the socket are in threaded engagement. The bushing may have an outer diameter small enough to prevent threaded engagement with the threads of the socket, such that movement of the ejector rod into the holder causes the bushing to come into rotational contact with the needle hub, thereby unthreading the needle hub from the socket and ejecting the needle assembly from the holder. Also, a spring may be received about the ejector rod and located on an opposite side of the internal rib from the bushing for biasing the ejector rod outward from the proximal end of the holder.

In a further embodiment, the present invention includes a holder for a disposable medical needle assembly. The holder includes an elongated holder body, an ejector rod cooperating with the holder body, a bushing received about the ejector rod, and a spring also received about the injector rod. The holder body includes a proximal end and a distal end, and defines an opening extending from the proximal end to the distal end. The distal end of the holder has a socket for receiving needle hub. The holder body defines an internal rib extending into the opening. The ejector rod extends into the opening from the proximal end of the holder body. The ejector rod is slidably received in the holder and has a distal end extending into the holder body. The ejector rod has a proximal end extending outward from the holder body. The bushing is received about the ejector rod and is located on a side of the internal rib facing the distal end of the holder body. The spring is received about the ejector rod and is located on an opposite side of the internal rib from the bushing for biasing the ejector rod outwardly from the proximal end of the holder body.

The holder may further include a button enclosing the proximal end of the ejector rod. The button may have a spring engaging end located within the holder for compressing the spring within the holder. Movement of the button into the holder may cause the ejector rod to contact the bushing such that the bushing comes into rotational contact with the needle hub and forcing the needle hub outward from the socket, thereby ejecting the needle assembly from the holder.

Further, an alternate embodiment of the medical needle device having a disposable needle assembly includes a holder, a needle assembly, an injector rod cooperating with the holder, a spring received about the ejector rod, and a button for operating the ejector rod. The button encloses the proximal end of the ejector rod and has a spring engaging end located within the holder for compressing the spring within the holder. Movement of the button into the holder causes the distal end of the ejector rod to force the needle hub outward from the socket, thereby ejecting the needle assembly from the holder.

Further details and advantages of the present invention will become apparent from the following detailed description read in conjunction with the drawings.

DETAILED DESCRIPTION

While this invention is discussed hereinafter in terms of several embodiments, the present disclosure is to be considered as exemplary of the principles of the invention and is not intended to limit the invention to the embodiments illustrated. Various modifications may be made to the present invention by those skilled in the art without departing from the scope and spirit of the present invention. The scope of the present invention is defined by the appended claims and their equivalents.

Figure 1:
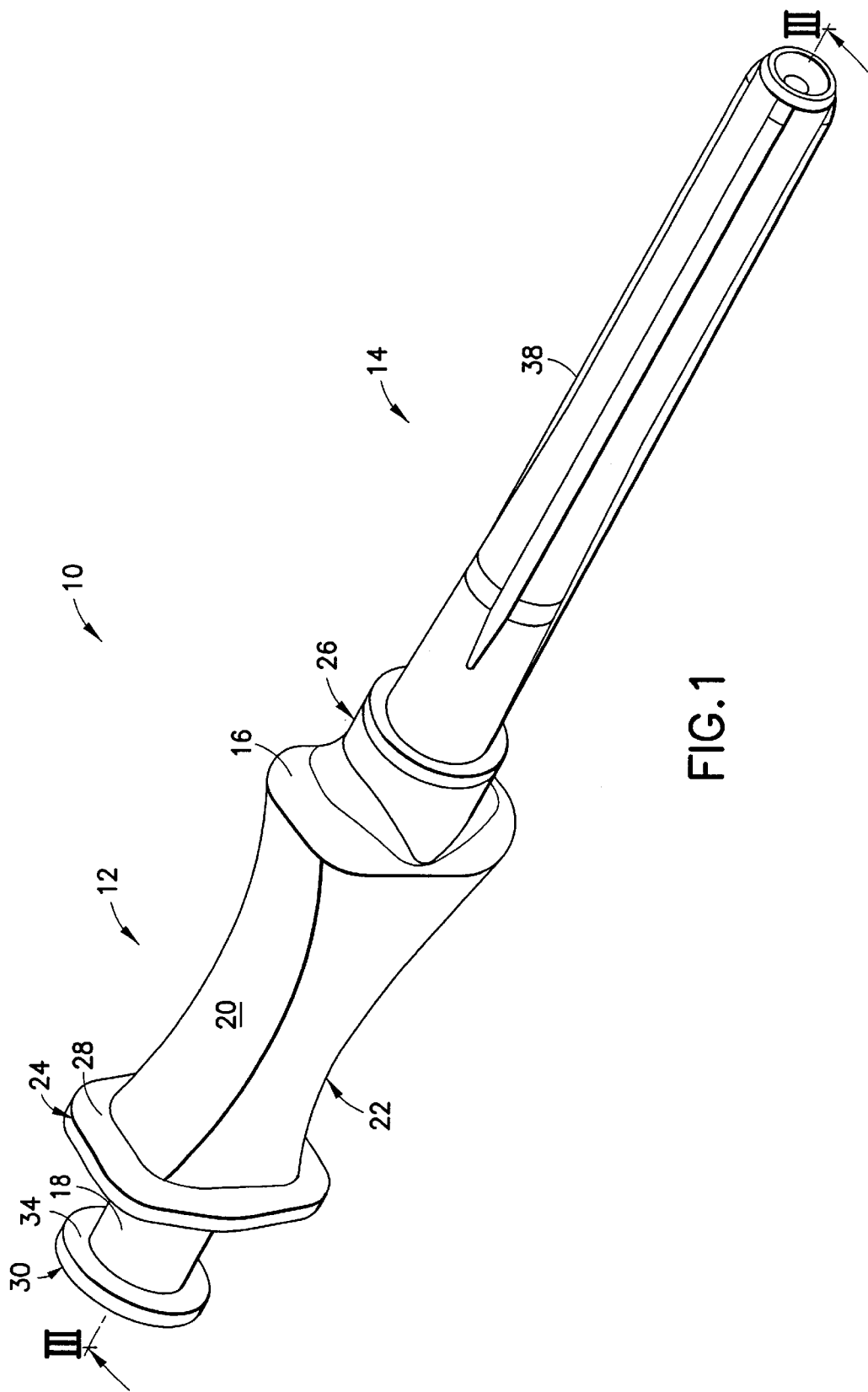
FIG. 1 is a perspective view of a unit dose needle device in accordance with a first embodiment of the present invention.
Figure 2:
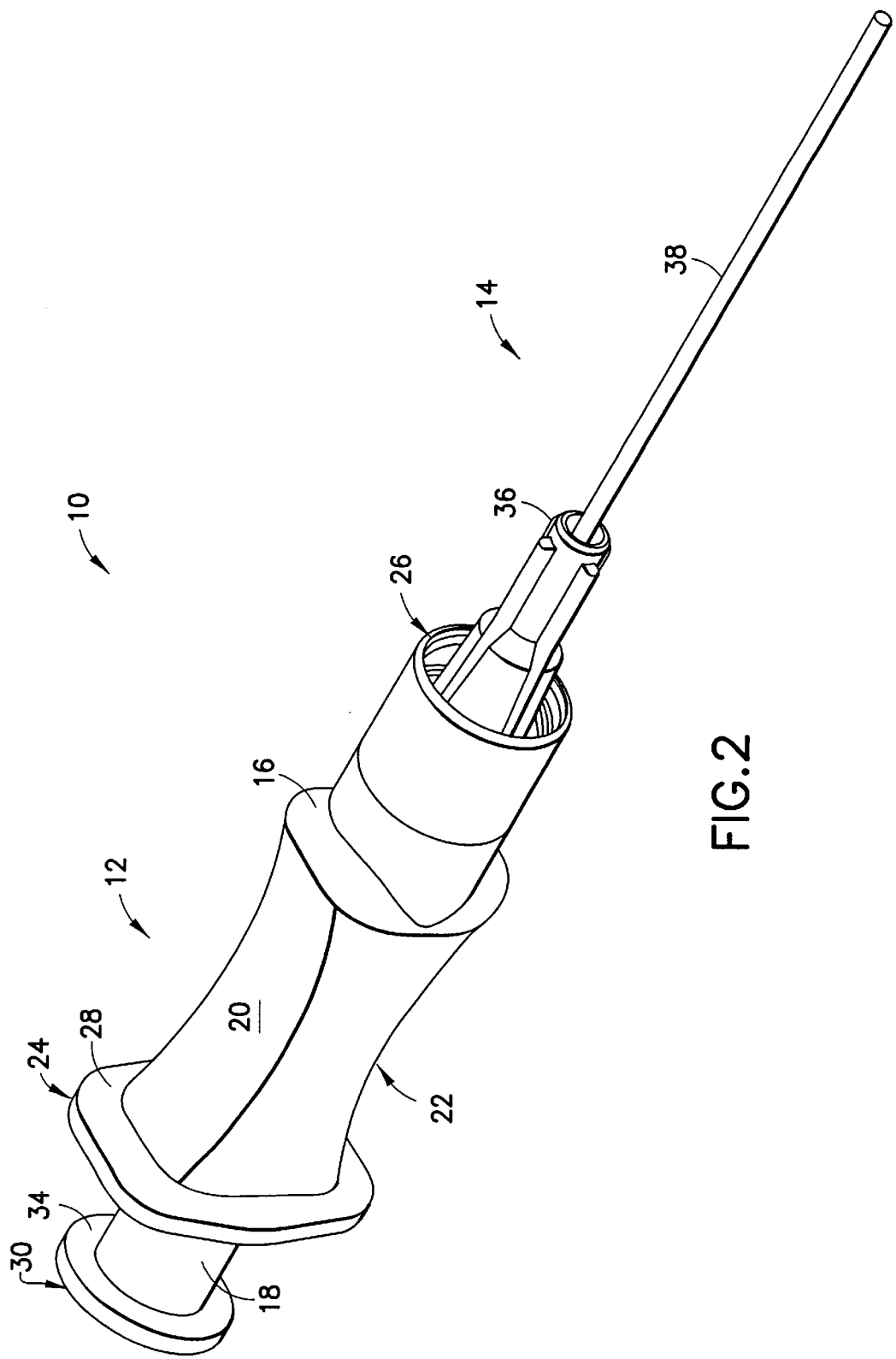
FIG. 2 is a perspective view of the unit dose needle device of FIG. 1 with the needle shield removed from the device.

In the following description and accompanying drawings the terms top and bottom refer to the orientation of a given element as shown in the drawings. Additionally, the terms distal and proximal refer to the forward end or needle side and the rearward end or holder side of the device, respectively. Referring to FIGS. 1 and 2, a first embodiment of a medical needle device 10 in the form of a unit dose needle device in accordance with the present invention is shown.

The medical needle device 10 includes a holder 12 and a needle assembly 14. The holder 12 includes a holder body 16. An ejector rod 18 extends into the holder body 16. The holder body 16 defines two convex surfaces 20, 22 at the top and bottom of the holder body 16, respectively, for grasping by a user of the medical needle device 10. The convex surfaces 20, 22 provide ergonomic grasping surfaces for the user of the medical needle device 10 to hold onto during a medical procedure. The holder body 16 includes a proximal end 24 and a distal end 26. The proximal end 24 of the holder body 16 forms a flange 28, which may be grasped by the user during a medical procedure. The holder body 16 is preferably formed as a one-piece unit and preferably molded of plastic material. The holder 12 is intended to be reused as discussed further herein. The ejector rod 18 includes a proximal end 30 extending outward from the holder body 16 and a distal end 32 (shown in FIG. 3) positioned within the holder body 16. A flange 34 is provided at the proximal end 30 of the ejector rod 18. The flange 34 facilitates directing the ejector rod 18 axially inward into the holder body 16, as discussed herein.

The needle assembly 14 further includes a needle hub 36 carrying a needle 38, and a needle shield 40 for covering the needle hub 34 and needle 36 prior to use. FIG. 1 shows the medical needle device 10 with the needle shield 40 covering the needle 38. In FIG. 2, the needle shield 40 has been removed, revealing the needle 38 and the needle hub 36.

Figure 3:
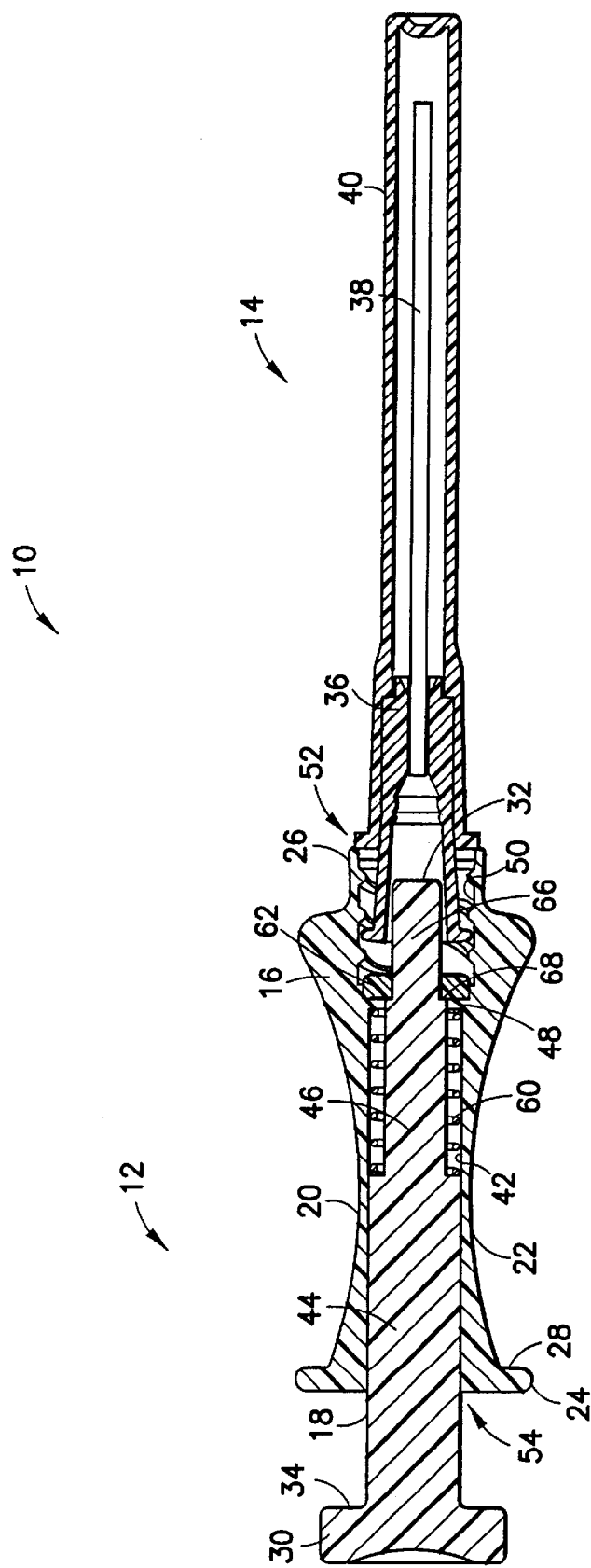
FIG. 3 is a cross-sectional view taken along line III—III in FIG. 1.
Figure 4:
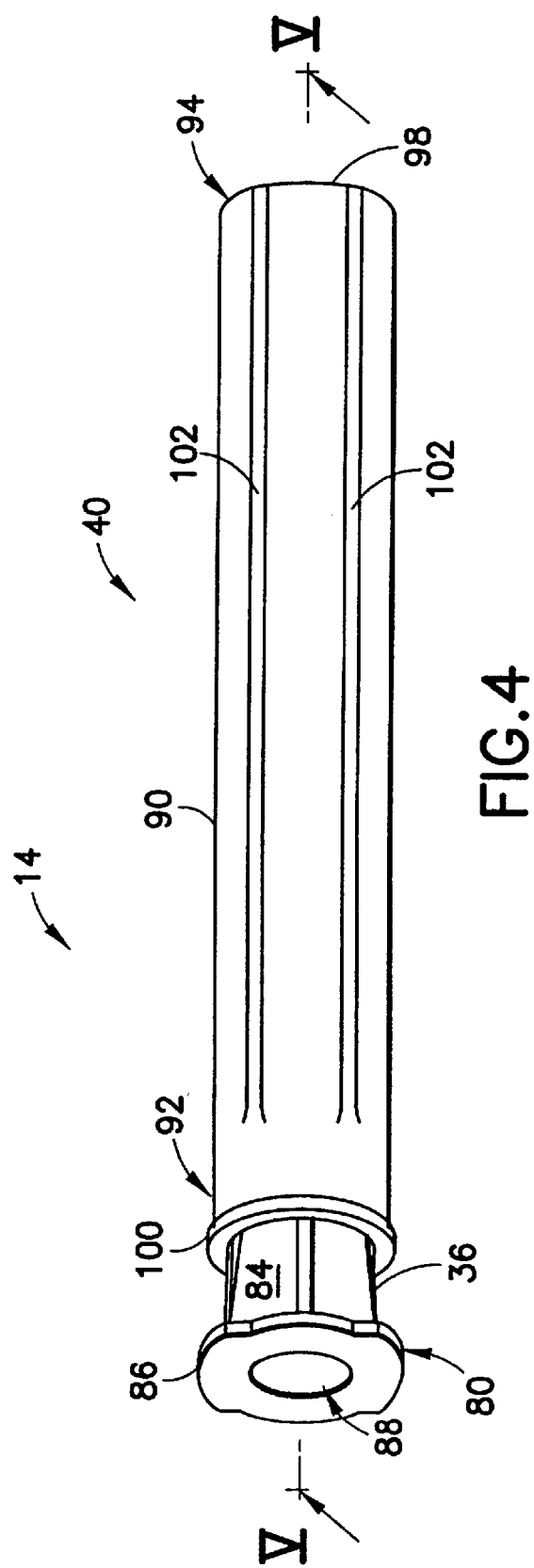
FIG. 4 is a side-perspective view of a needle assembly used in the unit dose needle device of FIG. 1.
Figure 5:
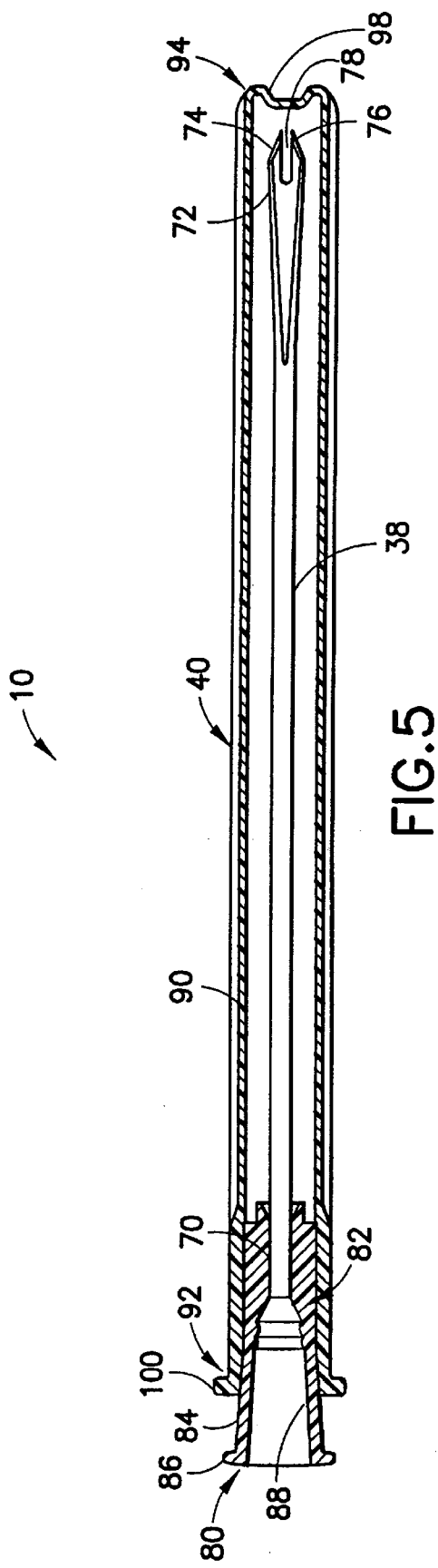
FIG. 5 is a cross-sectional view taken along line V—V in FIG. 4.
Figure 6:
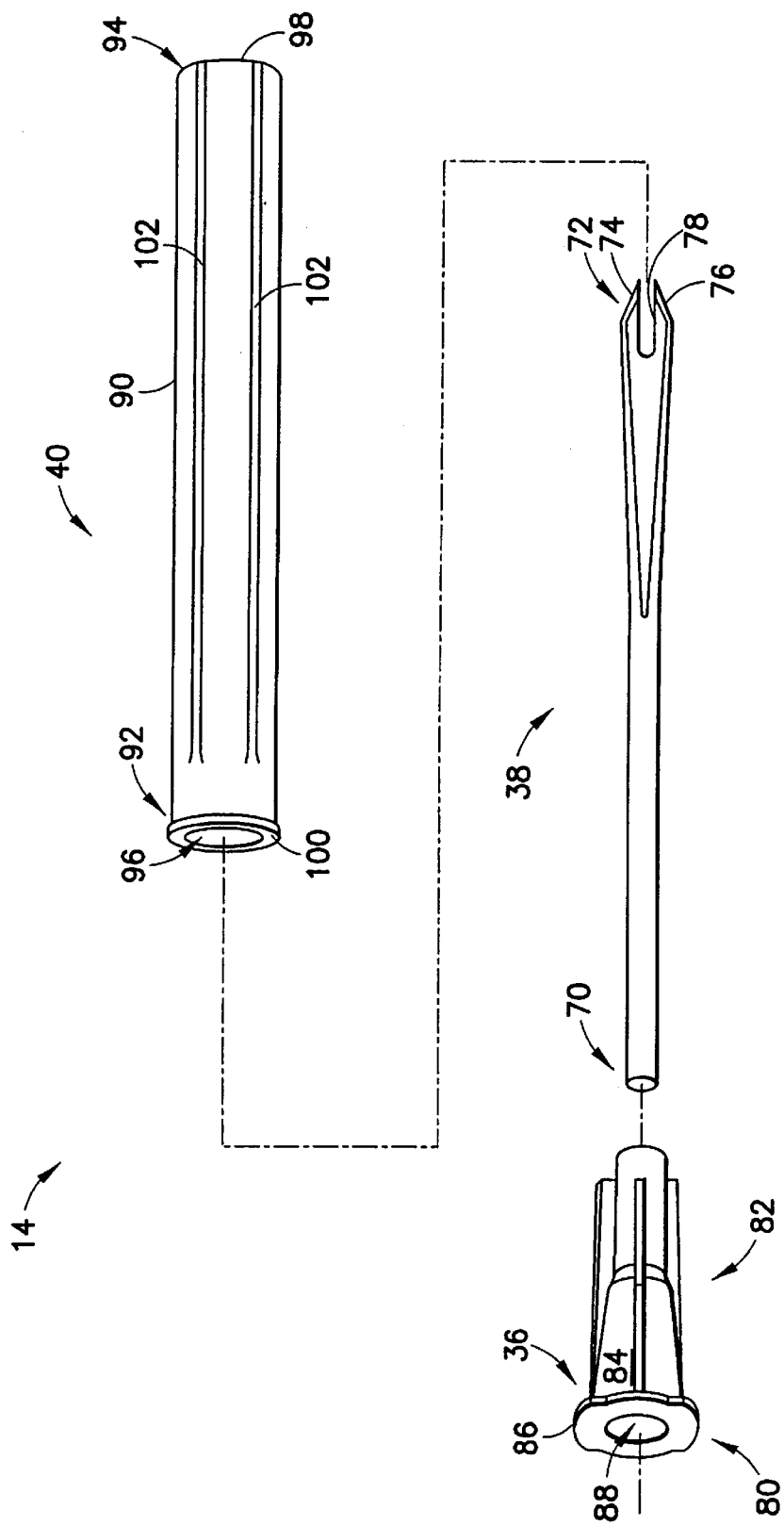
FIG. 6 is an exploded perspective view of the needle assembly of FIG. 4.
Figure 7:
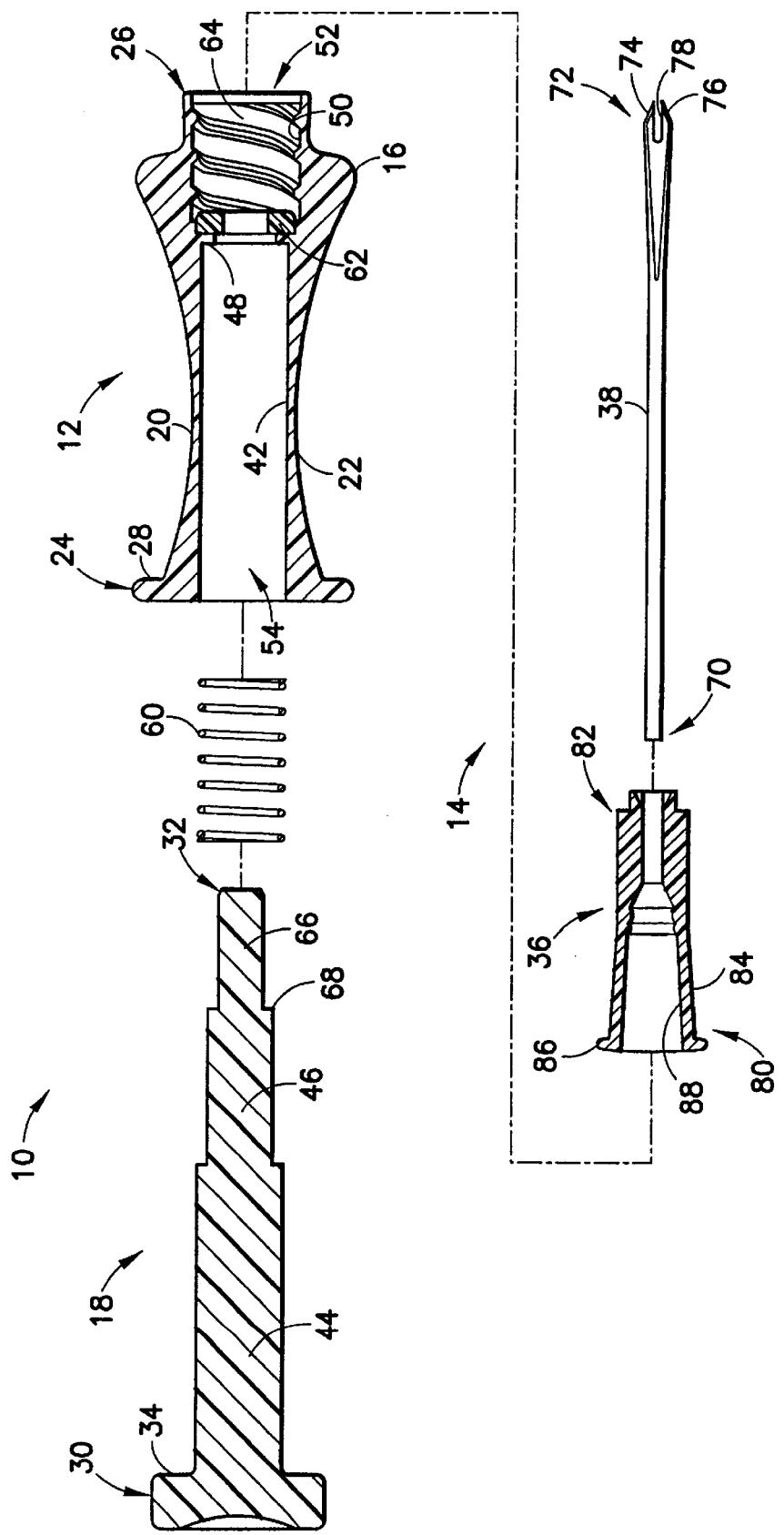
FIG. 7 is an exploded, cross-sectional view of the unit dose needle device of FIG. 2.

Referring to FIGS. 1–3, the medical needle device 10 will now be explained in greater detail. As shown in FIG. 3, the holder body 16 defines an opening 42 extending from the proximal end 24 to the distal end 26 of the holder body 16. The ejector rod 18 extends into the holder body 16 from the proximal end 24. The ejector rod 18 is preferably slidably received in the holder body 16. The ejector rod 18 includes its distal end 32 lying within the holder body 16, with the proximal end 30 extending outward from the holder body 16 so that the flange 34 is exposed. The ejector rod 18 is non-continuous in cross-section and generally includes a first portion 44 of greater diameter and a second portion 46 of smaller diameter, forming a shoulder therebetween.

The holder body 16 defines an internal rib 48, which generally separates the opening 42 into two portions. A first or distal portion 50 of the opening 42 is preferably internally threaded and forms a needle hub receiving socket 52. A second or proximal portion 54 of the opening 42 is smooth-walled and generally houses the first portion 44 of the ejector rod 18 having a larger diameter. The distal end 26 of the holder body 16 is generally cylindrically shaped and configured to receive the needle assembly 14 in the manner discussed hereinafter.

As stated, the ejector rod 18 extends into the holder body with its distal end 30 lying within the holder body 16. A spring 60 or other equivalent biasing means is received about the ejector rod 18 and located within the holder body. In particular, the spring 60 is received about the smaller diameter second portion 46 of the ejector rod 18 and is located on the proximal-facing side of the internal rib 48 formed in the opening 42. The spring 60 biases the ejector rod 18 outwardly from the holder body 16. The spring 60 is depicted in the figures as a coil spring, however, the spring 60 may comprise any resilient element capable of biasing the ejector rod 18 outward from to the holder body 16 at the proximal end 24 of the holder body 16. Therefore, if the ejector rod 18 is pushed into the holder body 16, the spring 60 provides a counteracting force for biasing the ejector rod 18 outward from the proximal end 24 of the holder body 16, to return the ejector rod to a pre-use configuration.

The holder 14 further includes a bushing 62 located within the holder body 16. The bushing 62 is received about the ejector rod 18 and lies on an opposite side of the internal rib 48 from the spring 60. The bushing 62 is located on the distal-facing side of the internal rib 48. The bushing 62 is generally located at the distal end 32 of the ejector rod 18. In particular, the ejector rod 18 further includes a third step down portion 66 of further reduced diameter, which defines an engaging lip 68 with the second portion 46. The engaging lip 68 is used to contact the proximal facing side of the bushing 62 to cause the bushing 62 to move toward the distal end 26 of the socket 52. Thus, the bushing 62 is generally positioned in the needle hub receiving socket 52 of the holder body 16. Generally, as discussed further hereinafter, when the ejector rod 18 is pushed a sufficient distance inward into the holder body 16, the bushing 62 will come into rotational contact with the hub 36 of the needle assembly 14. However, the bushing 62 is not in threaded engagement with the threads 64 of the socket 52.

Referring to FIGS. 3–6, the needle assembly 14 will now be discussed in greater detail. The needle assembly 14 includes the needle hub 36 and needle 38. The needle assembly 14 is generally a shielded, sterile, single-use unit that is disposable and removable from the holder 12. The needle assembly 14 further includes the needle shield 40 discussed previously. The needle 38 may be a conventional single-point needle, such as a hypodermic needle. However, the needle assembly 14 will be discussed hereinafter in terms of a preferred embodiment in the form of a unit dose needle assembly, including a unit dose needle, such as bifurcated needle 38. The needle assembly 14 is generally intended for use in the administration of vaccines applied to or through the skin of a patient. Thus, it is intended as a single-use, unit dose vaccination needle assembly including features to maintain sterility of the bifurcated needle 38 and to provide ease of use for the medical practitioner. The bifurcated needle 38, such as that shown, provides an efficient means for administration of a unit dose of vaccine, whether provided in a dry powder or liquid form, as is well-known in the art.

The bifurcated needle 38 includes a proximal end 70 and a distal end 72. The bifurcated needle 38 is provided with two sharp prongs 74, 76 at the distal end 72. A U-shaped channel 78 configured to hold a unit dose of vaccine separates the prongs 74, 76. The prongs are intended to penetrate or abrade the skin of the patient to administer the vaccine disposed in the U-shaped channel 78. The bifurcated needle may be constructed of any material known in the art, such as metal or plastic, and is desirably constructed of medical grade surgical steel.

The hub 36 is fixed to the proximal end 70 of the bifurcated needle 38, such as through an adhesive. The adhesive may be any adhesive capable of fixedly attaching or adhering the bifurcated needle 38 to the hub 36, such as a medical grade epoxy or equivalent adhesive. The hub 36 includes a proximal end 80 and a distal end 82, with the external surface of the hub 36 defining an outer tapered surface 84. The proximal end 80 of the hub 36 includes luer lugs 86 as a rim at the proximal end 80. The hub 36 defines an internal luer cavity 88, which tapers inward. The distal end 82 of hub 36 may include a bore having an internal diameter approximately the same size as the outer diameter of the proximal end 70 of the bifurcated needle 38 for accommodating and fixedly adhering the bifurcated needle 38 within hub 36.

The needle assembly 14 is provided with the needle shield 40 positioned over the bifurcated needle 38. The needle shield 40 is a generally tubular hollow construction and includes a tubular shield housing 90 extending between a proximal end 92 and a distal end 94 of the needle shield 40. The tubular shape of the housing 90 forms an internal opening 96 extending through the needle shield 40. The proximal end 92 of the needle shield 40 is generally open ended, forming a passage for accessing the internal opening 96, while the distal end 94 is closed ended forming an end wall 98. The needle shield 40 extends about the bifurcated needle 38 thereby containing the bifurcated needle 38 within the internal opening 96. The proximal end 92 includes a shield rim or lip 100 extending circumferentially about the open end. The proximal end 92 removably engages with the hub 36 along the tapered outer surface 84 of the hub 36 to form an airtight seal completely concealing the bifurcated needle 38 and associated prongs 74, 76 in a sterile, airtight manner. The needle shield 40 serves to protect the bifurcated needle 38 from damage and exposure during shipping and storage, and prior to the insertion of the needle assembly 14 into the holder 12. The needle shield 40 also provides protection to medical personnel from needle sticks prior to removing the needle shield 40 for use.

The hub 36 and needle shield 40 may be constructed of any material, and are desirably constructed of a moldable plastic material. Suitable moldable plastics include, but are not limited to, polyethylenes, polypropylenes, polyamides, polyesters, and fluorinated polyethylenes, which may also be used to form the holder body 16 and ejector rod 18. The needle shield 40 may further include external ribs 102 integrally molded with the shield housing 90 and extending longitudinally along the outer surface of the shield housing 90 between the proximal end 92 and the distal end 94. The external ribs 102 provide further structural integrity to the needle shield 40, which is particularly useful during packaging and storage to maintain shape.

The bifurcated needle 38 is generally operable with vaccines that are provided in any suitable form. Suitable physical forms for the vaccine include, but are not limited to, liquids such as solutions, emulsions, and dispersions, or dry powders. Typically, the bifurcated needle 38 will be used with a vaccine that is in liquid form. Moreover, the vaccine is desirably associated with the needle assembly 14 during storage, and may therefore be maintained within the U-shaped channel 78 prior to removal of the needle shield 40. Alternatively, the vaccine may be provided as a separate component, with the bifurcated needle 38 being contacted with the vaccine after removing the needle shield 40 just prior to use of the needle assembly 14 with the holder for the administration of the vaccine.

As noted, the needle shield 40 sealingly mates with the hub 36 to provide an airtight connection therebetween, with the bifurcated needle 38 contained within the airtight environment in the internal opening 96 of the needle shield 40. Such an airtight arrangement provides the needle assembly 14 as a self-contained assembly, in the form of a complete, shielded, sterile, single-use unit, which may be inserted into the holder 12. The holder 12 and the needle assembly 14 may be packaged separately, and assembled just prior to use. As such, the present invention envisions that multiple needle assemblies 14 may be used with the reusable holder 12, with the needle assembly 14 discarded after use.

Operation of the medical needle device 10 will be discussed hereinafter in connection with FIGS. 1–7. To use the medical needle device 10, the user first removes the needle assembly 14 from a suitable sterile package. The hub 36 of the needle assembly 14 is inserted into the socket 52 in the holder body 16. The hub 36 preferably has an outer diameter sized to be threadably received within the socket 52. In particular, luer lugs 86 of the hub 36 are sized to be threadably received in the threads formed in the socket 52. The shield rim 100 of the needle shield 40 engages or cooperates with the distal end 26 of the holder body 16. Preferably, the outer diameter of the shield rim 100 is the same size or larger than the outer diameter of the distal end 26 of the holder body 16 such that the needle shield 40 is not inserted into the socket 52. The shield rim 100 engages the distal end 26 of the holder body 16.

The user of the medical needle device 10 threads the hub 36 into the socket 52. As the hub 36 or, more particularly, the luer lugs 86 are threaded into the socket 52, the needle shield 40 is forced outwardly from the hub 36 by the contact between the shield rim 100 and the distal end 26 of the holder body 16. As luer lugs 86 are threaded further into the socket 52, the needle shield 40 is forced outward and out of contact with the hub 36 and the needle shield 40 spins freely upon the hub 36 for easy removal in preparation of use of the bifurcated needle 38.

The user of the medical needle device 10 may then remove the needle shield 40 and perform a vaccination procedure. As discussed previously, the vaccine may be provided separately from the bifurcated needle, or the vaccine may be associated with the bifurcated needle 38 during storage and contained within the U-shaped channel 78 prior to removal of the needle shield 40. Once the vaccination procedure is performed, the needle assembly 14 may be disposed of in a medical waste container such as a SHARPS container. This procedure is performed as follows: the distal end 32 of the ejector rod 18 facilitates removal of the needle assembly 14 from the holder body 16. In particular, to remove the needle assembly 14, the user of the medical needle device 10 pushes on the proximal end 30 of the ejector rod 18 such that the ejector rod 18 progresses axially into the opening 42 in the holder body 16. The spring 60 is compressed between the shoulder of the larger diameter first portion 44 of the ejector rod 18 and the internal rib 48 formed within the opening 42. As the ejector rod 18 progresses into the opening 42, the engaging lip 68 contacts and engages the proximal facing side of the bushing 62, which causes the bushing 62 to progress toward the distal end 26 of the holder body 16 and come into rotatable contact with the luer lugs 86. By depressing the ejector rod 18 a sufficient distance inwardly into the holder body 16, the bushing 62 will force the luer lugs 86 to progress outward from the socket 52. In particular, the luer lugs 86 are unthreaded from the socket 52 and expelled from the holder body 16. The pitch of the threads within the socket 52 has a sufficient coarseness to retain the luer lugs 86 in the socket 52, but not lock the luer lugs 86 against a face of the threads within the socket 52 when the hub 36 is acted upon by the bushing 62. In this manner, the needle assembly 14 is ejected from the holder body 16 and a new needle assembly 14 may be inserted into the holder body 16 to perform another vaccination procedure.

Figure 8:
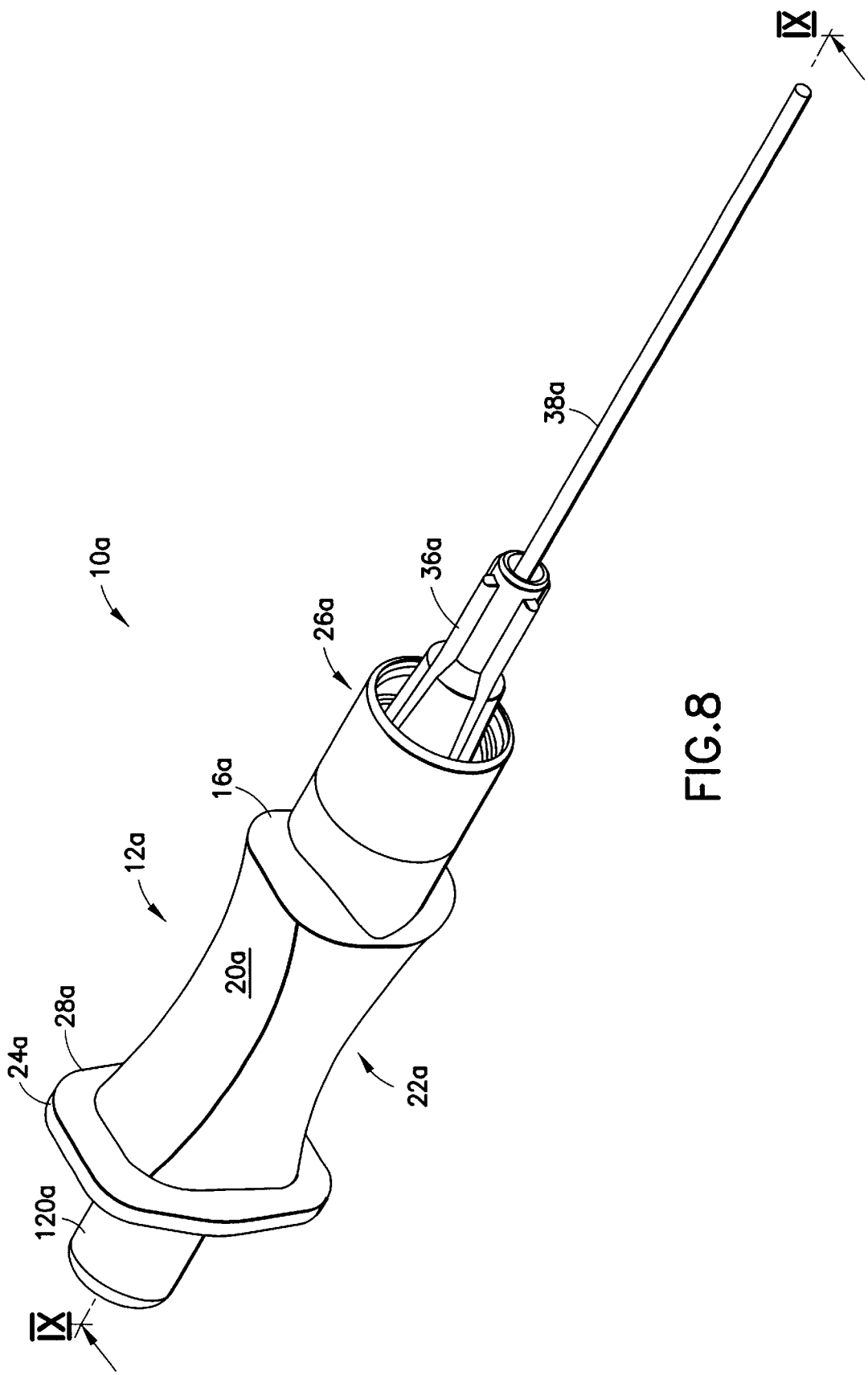
FIG. 8 is a perspective view of the unit dose needle device of FIG. 1 according to a second embodiment of the present invention, with the needle shield removed from the device.
Figure 9:
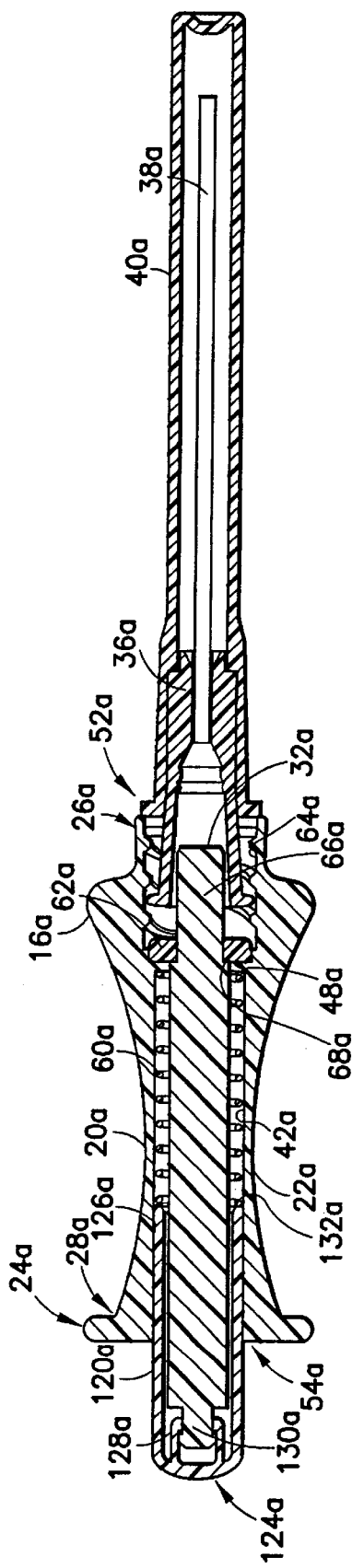
FIG. 9 is a cross-sectional view taken along line IX—IX in FIG. 8.
Figure 10:
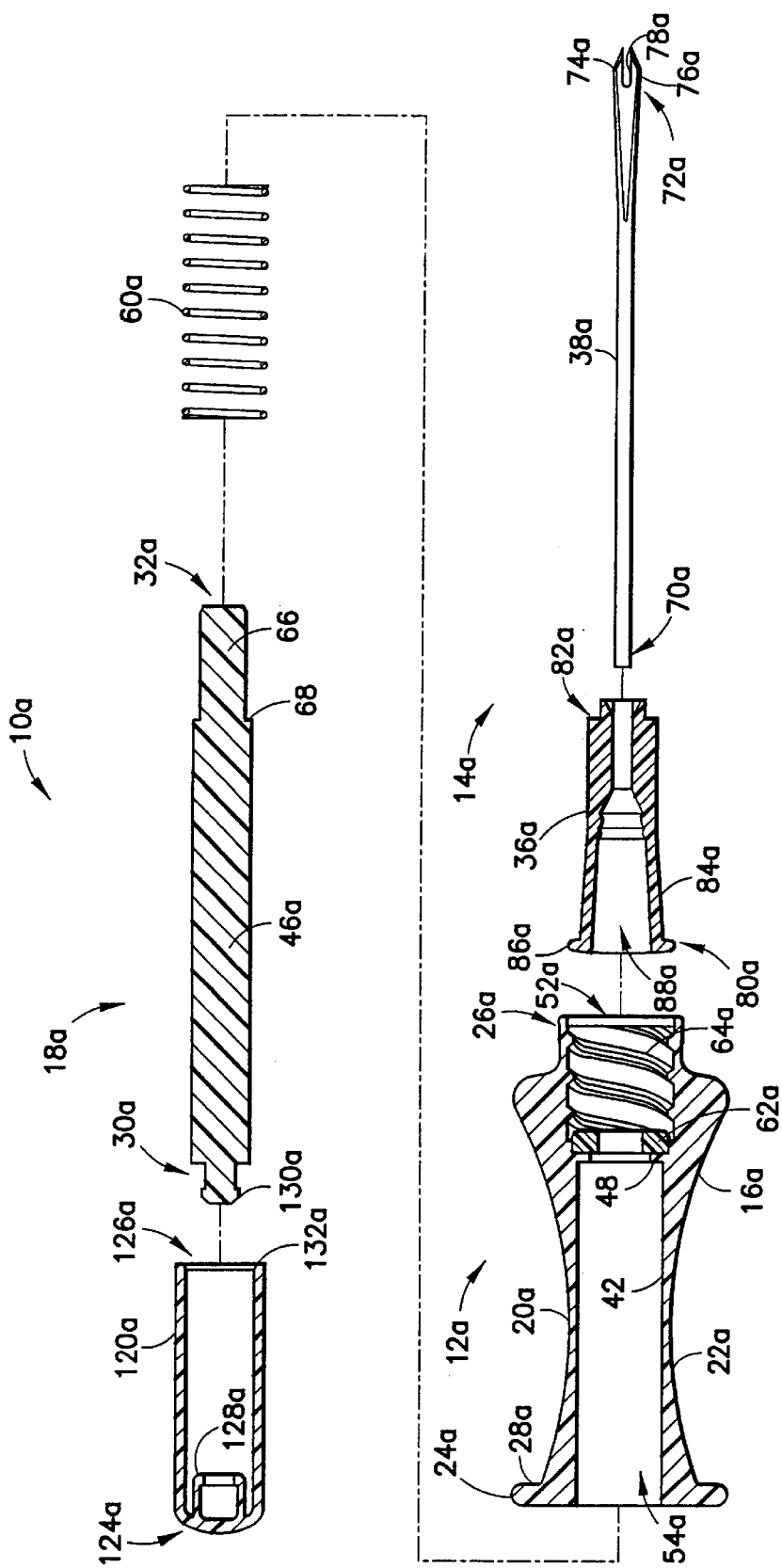
FIG. 10 is an exploded, cross-sectional view of the unit dose needle device of FIG. 8.

A second embodiment of the medical needle device of the present invention is shown in FIGS. 8–10. The medical needle device of FIGS. 8–10 is substantially similar to the medical needle device 10 discussed previously in connection with FIGS. 1–7, and like parts are identified with like reference numerals, except that a suffix "a" will be used to identify those similar components in FIGS. 8–10.

The differences between the medical needle device 10a shown in FIGS. 8–10 and that discussed previously are two-fold. First, the medical needle device 10a of this embodiment includes a modified ejector rod 18a. The ejector rod 18a has a button 120a fixed to the proximal end 30a of the ejector rod 18a, preferably through a snap-fit or equivalent lockable connection as shown. In particular, the button 120a is cylindrically shaped and has a closed end 124a and an open end 126a. A connection flange 128a extends from the inner surface of the closed end 124a. The ejector rod 18a further includes a connecting member 130a adapted to snap-fit with the connection flange 128a, as shown in FIG. 9. The button 120a includes a spring engagement surface 132a formed the opened end 124a for compressing the spring 60a against the internal rib 48a in the opening 42a defined through the holder body 16a. Thus, the ejector rod 18a is biased outward from the proximal end 24a of the holder body 16a by the spring 60a in a similar manner to the medical needle device 10 of FIGS. 1–7. The button 120a is slidable along the inner surface of the opening 42a with the ejector rod 18a.

In addition, the ejector rod 18a is slightly modified. The larger diameter first portion 44 is eliminated. Thus, the second portion 46a forms the largest diameter portion of the ejector rod 18a. The engaging lip 68a is formed between the second portion 46a and stepped down portion 66a on the ejector rod 18a.

The user of the medical needle device 10a shown in FIGS. 8–10 will operate the device in the same manner discussed previously, with the exception that the user will depress the button 120a into the holder body 16a, which will compress the spring 60a in the holder body 16a. When the button 120a is released, the spring 60a will bias the button 120a outward from the proximal end 24a of the holder body 16a. The needle assembly 14a is ejected from the medical needle device 10a of FIGS. 8–10 in a similar manner to the medical needle device 10 discussed previously in connection with FIGS. 1–7. Replaceable needle assemblies 14a may be used when the holder 12a is reduced in subsequent vaccination procedures.

As discussed above, by providing the holder and the needle assembly as separate members which can attached needle assemblies can be separately packaged in sterile packaging, and the holder can be used with multiple needle assemblies which are discarded after each use thereof. Moreover, the holder provides an effective handle for the needle assembly, which is particularly useful for the administration of a vaccine to a patient. Thus, the reusable holder provides an effective handle for manipulation and use of a needle, and provides a mechanism for ejecting and discarding a used needle.

What is claimed is:

1. A medical needle device, comprising:

a holder having a proximal end, a distal end, and an opening extending from the proximal end to the distal end, with the distal end of the holder having a needle hub receiving socket;

a needle assembly comprising a needle hub and a needle, with the entirety of the proximal end of the needle hub received entirely in the socket of the holder; and an ejector rod extending into the opening through the proximal end of the holder, with the ejector rod slidably received in the holder and having a distal end configured to engage the needle hub and a proximal end extending outward from the holder, wherein movement of the ejector rod into the holder causes the distal end of the ejector rod to force the needle hub outward from the socket thereby ejecting the needle assembly from the holder.

2. The medical device of claim 1, wherein the needle is a bifurcated needle.

3. The medical needle device of claim 2, wherein a proximal end of the needle hub defines a luer cavity.

4. The medical needle device of claim 1, wherein the holder defines an internal rib extending into the opening, and wherein a bushing is adjacent the distal end of the ejector rod between the needle hub and internal rib.

5. The medical needle device of claim 4, wherein the needle hub and socket are in threaded engagement, wherein the bushing has an outer diameter small enough to prevent threaded engagement with the threads of the socket, and wherein movement of the ejector rod into the holder causes the bushing to come into rotational contact with the needle hub thereby unthreading the needle hub from the socket and ejecting the needle assembly from the holder.

6. The medical needle device of claim 5, wherein the needle hub includes a luer lock and the socket is internally threaded such that the luer lock is in threaded engagement in the socket.

7. The medical needle device of claim 5, further comprising a spring received about the ejector rod and located on an opposite side of the internal rib from the bushing for biasing the ejector rod outward from the holder.

8. The medical needle device of claim 1, wherein the outer surface of the holder defines two convex surfaces for grasping by the user of the medical needle device.

9. The medical needle device of claim 1, further comprising a removable needle shield covering the needle.

10. The medical needle device of claim 9, wherein the needle shield includes a shield rim cooperating with the needle hub, and wherein the shield rim is sized such that when the needle assembly is inserted into the holder the shield rim contacts the distal end of the holder and is automatically forced outward from the needle hub.

11. The medical needle device of claim 1, wherein the proximal end of the holder defines a flange for grasping by the user of the device.

12. A holder for a disposable medical needle assembly, comprising:

an elongated holder body having a proximal end and a distal end and defining an opening extending from the proximal end to the distal end, with the distal end of the holder body having a needle hub receiving socket, and with the holder body defining an internal rib extending into the opening;

an ejector rod extending into the opening from the proximal end of the holder body, with the ejector rod slidably received in the holder and having a distal end extending into the holder body and a proximal end extending outward from the holder body;

a bushing adjacent the distal end of the ejector rod and located on a side of the internal rib facing the distal end of the holder body; and a spring received about the ejector rod and located on an opposite side of the internal rib from the bushing for biasing the ejector rod outwardly from the holder body.

13. The holder of claim 12, wherein the needle hub receiving socket is internally threaded.

14. The holder of claim 13, wherein the bushing has an outer diameter small enough to prevent threaded engagement with the threads of the socket.

15. The holder of claim 12, wherein the outer surface of the holder defines two convex surfaces for grasping by the user of the medical needle device.

16. The holder of claim 12, wherein the proximal end of the holder defines a flange for grasping by the user of the device.

17. The holder of claim 12, further comprising a button enclosing the proximal end of the ejector rod and having a spring-engaging end located within the holder for compressing the spring within the holder, wherein movement of the button into the holder causes the ejector rod to contact the bushing such that the bushing comes into contact with the needle hub and forces the needle hub outward from the socket thereby ejecting the needle assembly from the holder.

18. A medical needle device, comprising:

a holder having a proximal end and a distal end and defining an opening extending from the proximal end to the distal end, and with the distal end of the holder having a needle hub receiving socket;

a needle assembly comprising a needle hub and a needle, with the needle hub received in the socket;

an ejector rod extending into the opening through the proximal end of the holder, with the ejector rod slidably received in the holder and having a distal end configured to engage the needle hub and a proximal end extending outward form the holder;

a spring received about the ejector rod and located within the holder for biasing the ejector rod outwardly from the holder; and a button enclosing the distal end of the ejector rod and having a spring-engaging end located within the holder for compressing the spring within the holder, wherein movement of the button into the holder causes the distal end of the ejector rod to force the needle hub outward from the socket thereby ejecting the needle assembly from the holder.

19. The medical needle device of claim 18, wherein the needle is a bifurcated needle.

20. The medical needle device of claim 19, wherein a proximal end of the needle hub defines a luer cavity.

21. The medical needle device of claim 18, wherein the holder defines an internal rib extending into the opening, and wherein a bushing is adjacent the distal end of the ejector rod between the needle hub and internal rib.

22. The medical needle device of claim 21, wherein the needle hub and socket are in threaded engagement, wherein the bushing has an outer diameter small enough to prevent threaded engagement with the threads of the socket, and wherein movement of the ejector rod into the holder causes the bushing to come into rotational contact with the needle hub thereby unthreading the needle hub from the socket and ejecting the needle assembly from the holder.

23. The medical needle device of claim 22, wherein the needle hub includes a luer lock and the socket is internally threaded such that the luer lock is in threaded engagement in the socket.

24. The medical needle device of claim 22, wherein the spring received about the ejector rod is located on an opposite side of the internal rib from the bushing for biasing the ejector rod outward from the holder.

25. The medical needle device of claim 18, wherein the outer surface of the holder defines two convex surfaces for grasping by the user of the medical needle device.

26. The medical needle device of claim 18, further comprising a removable needle shield covering the needle.

27. The medical needle device of claim 26, wherein the needle shield includes a rim cooperating with the needle hub, and wherein the shield rim is sized such that when the needle assembly is inserted into the holder the shield rim contacts the distal end of the holder and is automatically forced outward from the needle hub.

* * * * *